US012728150B2

(12) United States Patent
Seki

(10) Patent No.: US 12,728,150 B2
(45) Date of Patent: Sep. 8, 2026

(54) COMBINATION PHARMACEUTICAL OF TEMOZOLOMIDE AND MUTANT IDHI ENZYME INHIBITOR

(71) Applicant: DAIICHI SANKYO COMPANY, LIMITED, Tokyo (JP)

(72) Inventor: Takahiko Seki, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 754 days.

(21) Appl. No.: 18/016,540

(22) PCT Filed: Jul. 20, 2021

(86) PCT No.: PCT/JP2021/027070

§ 371 (c)(1),
(2) Date: Jan. 17, 2023

(87) PCT Pub. No.: WO2022/019289

PCT Pub. Date: Jan. 27, 2022

(65) Prior Publication Data

US 2023/0270814 A1 Aug. 31, 2023

(30) Foreign Application Priority Data

Jul. 21, 2020 (JP) ................................. 2020-124331

(51) Int. Cl.
*A61K 38/00* (2006.01)
*A61K 31/495* (2006.01)
*A61P 35/00* (2006.01)

(52) U.S. Cl.
CPC .......... *A61K 38/005* (2013.01); *A61K 31/495* (2013.01); *A61P 35/00* (2018.01)

(58) Field of Classification Search
CPC .... A61K 38/005; A61K 31/495; A61K 45/06; A61K 31/4184; A61K 31/422; A61K 31/444; A61K 31/4709; A61K 31/506; A61K 31/53; A61K 31/4188; A61K 31/42; A61K 31/4545; A61K 45/00; A61P 35/00; A61P 35/02; A61P 43/00
See application file for complete search history.

(56) References Cited

U.S. PATENT DOCUMENTS

| | | | |
|---|---|---|---|
| 3,336,307 | A | 8/1967 | Shen |
| 7,812,017 | B2 | 10/2010 | Angbrant et al. |
| 8,637,537 | B2 | 1/2014 | Aliagas-Martin et al. |
| 9,120,780 | B2 | 9/2015 | Kitade et al. |
| 9,505,755 | B2 | 11/2016 | Adams et al. |
| 9,662,327 | B2 | 5/2017 | Cao et al. |
| 9,856,279 | B2 | 1/2018 | Cao et al. |
| 10,040,791 | B2 | 8/2018 | Saito et al. |
| 2003/0130525 | A1 | 7/2003 | Kwak et al. |
| 2013/0184222 | A1 | 7/2013 | Popovici-Muller et al. |
| 2017/0313696 | A1* | 11/2017 | Saito .................... A61K 31/454 |
| 2023/0382856 | A1 | 11/2023 | Sakurai et al. |

FOREIGN PATENT DOCUMENTS

| | | | |
|---|---|---|---|
| CN | 103764658 | | 4/2014 |
| CN | 104230781 | A | 12/2014 |
| CN | 106565683 | A | 4/2017 |
| EP | 2721033 | | 4/2014 |
| EP | 3105209 | | 12/2016 |
| EP | 3202766 | | 8/2017 |
| GB | 2284600 | A | 6/1995 |
| JP | 2009541461 | A | 11/2009 |
| JP | 2011057594 | A | 3/2011 |
| JP | 2013536168 | A | 3/2013 |
| JP | 2014519518 | A | 8/2014 |
| JP | 2014521607 | A | 8/2014 |
| JP | 2014524456 | A | 9/2014 |
| JP | 2019-094299 | | 6/2019 |
| JP | 2019094299 | A * | 6/2019 |
| JP | 2019131672 | A | 8/2019 |
| WO | WO 94/10145 | A1 | 5/1994 |
| WO | WO 94/24095 | A1 | 10/1994 |
| WO | WO 2004072051 | A1 | 8/2004 |
| WO | WO 2012093707 | A1 | 7/2012 |
| WO | WO 2012171506 | A1 | 12/2012 |
| WO | WO 2012173682 | A2 | 12/2012 |
| WO | WO 2013046136 | A1 | 4/2013 |
| WO | WO 2013/107291 | | 7/2013 |
| WO | WO 2013107405 | A1 | 7/2013 |
| WO | WO 2014/141104 | | 9/2014 |
| WO | WO 2015/003640 | | 1/2015 |
| WO | WO 2015066344 | A1 | 5/2015 |
| WO | WO 2015/121210 | | 8/2015 |
| WO | WO 2016/044787 | | 3/2016 |
| WO | WO 2016/052697 | | 4/2016 |

(Continued)

OTHER PUBLICATIONS

Stupp (The Lancet Oncology, Sep. 2001, vol. 2, 552-560) (Year: 2001).*

Office Action in JP Appln. No. 2021119216, mailed on Jul. 31, 2025, with English Translation, 12 pages.

ClinicalTrials.gov Identifier: NCT04603001, "Study of Oral LY3410738 in Patients With Advanced Hematologic Malignancies With IDH1 or IDH2 Mutations," Dec. 1, 2020, retrieved on May 11, 2023, retrieved from URL <https://clinicaltrials.gov/ct2/show/NCT04603001>, 5 pages.

GenBank Accession No. NP 005887.2, "Isocitrate dehydrogenase [NADP] cytoplasmic," Jul. 10, 2019, 4 pages.

International Search Report and Written Opinion in International Appln. No. PCT/JP2021/027070, mailed on Sep. 28, 2021, 12 pages.

(Continued)

*Primary Examiner* — Sudhakar Katakam

(74) *Attorney, Agent, or Firm* — Fish & Richardson P.C.

(57) ABSTRACT

By combining temozolomide with a mutant IDH1 enzyme inhibitor, it was discovered that the dosage of temozolomide could be reduced without decreasing the antitumor effect, enabling us to provide a combination drug with excellent efficacy against cancers with IDH1 mutations.

10 Claims, 1 Drawing Sheet

(56) References Cited

FOREIGN PATENT DOCUMENTS

| WO | WO 2017/016992 | 2/2017 |
|---|---|---|
| WO | WO 2018/231799 | 12/2018 |

OTHER PUBLICATIONS

Japan Registry of Clinical Trials, Clinical Research Submission and Publication System No. jRCT2031200178, "A Phase I Study of LY1 in Patients With Advanced Solid Cancer with IDH2 or IDH3410738 Mutations," Oct. 28, 2020, 4 pages.
Momota et al, "Secondary hematological malignancies associated with temozolomide in patients with glioma," Neuro Oncol., Mar. 2013, 15(10):1445-1450.
Tateishi, "Synergistic approach to enhance DNA damage for IDHI mutant cancers," SGH Cancer Research Reports, Mar. 2020, 30:61-66.
UniProt Accession No. O75874, "Isocitrate dehydrogenase [NADP] cytoplasmic," Jul. 3, 2019, 13 pages.
Kaminska et al., "Consequences of IDH1/2 Mutations in Gliomas and an Assessment of Inhibitors Targeting Mutated IDH Proteins," Molecules, Mar. 2019, 24:968, 17 pages.
Kogiso et al., "Abstract 4031: Mutant isocitrate dehydrogenase 1 (IDH1) inhibitor synergistically prolongs animal survival with standard therapies in patient-derived IDHI mutant glioma xenograft mouse models," Cancer Research, Jul. 2017, 77:(Supplement 13):4031.
Extended European Search Report in European Appln No. 21845205.0, dated Dec. 11, 2023, 17 pages.
Amary et al., "Ollier Disease and Maffucci Syndrome Are Caused by Somatic Mutations of IDH1 and IDH2," Nature Genetics, Dec. 2011, 43(12):1262-1266.
Ashizawa, "Evaluation of physical properties of molecular state of pharmaceutical crystals (12) Optimization of salt and crystal forms and crystallization technology," Pharm Tech Japan, Sep. 2002, 18(10):81-96, 34 pages (with machine translation).
Bai et al., "Organocatalytic Formal (3 + 2) Cycloaddition toward Chiral Pyrrolo[1,2-a]indoles via Dynamic Kinetic Resolution of Allene Intermediates," Organic Letters, Jun. 2020, 22(14):5439-5445.
Borger et al., "Frequent Mutation of socitrate Dehydrogenase (IDH) 1 and IDH2 in Cholangiocarcinoma identified Through Broad-Based Tumor Genotyping," Oncologist, 17(1):72-79, 2012.
Cairns et al., "IDH2 Mutations Are Frequent in Angioimmunoblastic T-Cell Lymphoma," Blood, 119(8):1901-1903, Feb. 2012.
Chen et al., "Asymmetric Synthesis of Furo[3,4-b]indoles by Catalytic [3+2] Cycloaddition of Indoles with Epoxides," Chemistry: A European Journal, Sep. 2015, 21(43):15104-15107.
Dang, L. et al., "Cancer-Associated IDHI Mutations Produce 2-Hydroxyglutarate," Nature, 462(7274):739-744, Dec. 2009.
Database Registry, RN 443778-21-0, Aug. 2002, Chemical Library, 1 page.
Database Registry, RN 732270-62-1, Aug. 2004, Chemical Library, 1 page.
Duan et al., "Synthesis of Pyrido[2,3-b]indole Derivatives via Rhodium-Catalyzed Cyclization of Indoles and 1-Sulfonyl-1,2,3-triazoles," Advanced Synthesis & Catalysis, Mar. 2020, 362(9):1831-1835, 6 pages.
Gross et al., "Cancer-Associated Metabolite 2-Hydroxyglutarate Accumulates in Acute Myelogenous Leukemia With lsocitrate Dehydrogenase 1 and 2 Mutations," Journal of Experimental Medicine, 207(2):339-344, Feb. 2010.
Harada et al., "Generation and reactions of low-valent titanium alkoxide-acetylene complexes. A practical preparation of allyl alcohols," Tetrahedron Letters, May 1995, 36(18):3203-3206.
Hemerly et al., "Identification of Several Novel Non-p.R132 IDHI Variants in Thyroid Carcinomas," European Journal of Endocrinology, 163(5):747-755, Nov. 2010.
International Preliminary Report on Patentability in International Appln. No. PCT/JP2021/027070, mailed on Jan. 24, 2023, 5 pages.
Kang et al., "Mutational Analysis of IDHI Codon 132 in Glioblastomas and Other Common Cancers," International Journal of Cancer, 125(2):353-355, Jul. 2009.
Kosmider et al., "Mutations of IDHI and IDH2 Genes in Early and Accelerated Phases of Myelodysplastic Syndromes and MDS/Myeloproliferative Neoplasms," Leukemia, 24(5):1094-1096, May 2010.
Liu et al., "Isocitrate Dehydrogenase 2 Mutation Is a Frequent Event in Osteosarcoma Detected by a Multi-Specific Monoclonal Antibody MsMab-1," Cancer Medicine, 2(6):803-814, Dec. 2013.
Losman et al., "(R)-2-Hydroxyglutarate Is Sufficient to Promote Leukemogenesis and Its Effects Are Reversible," Science, 339(6127):1621-1625, Mar. 2013.
Mardis et al., "Recurring Mutations Found by Sequencing an Acute Myeloid Leukemia Genome," New England Journal of Medicine, 36(11):1058-1066, Sep. 2009.
Nakagawa et al., "Selective inhibition of mutant IDHI by DS-1001b ameliorates aberrant histone modifications and impairs tumor activity in chondrosarcoma," Oncogene, Oct. 2019, 38(42):6835-6849.
Office Action in CN Appln. No. 202180060294.5, mailed on Aug. 18, 2025, 21 pages, with English Translation.
Office Action in CN Appln. No. 202180060294.5, mailed on Mar. 19, 2025, 19 pages, with English Translation.
Office Action in CN Appln. No. 202180060294.5, mailed on Oct. 11, 2024, 18 pages, with English Translation.
Office Action in EP Appln. No. 21845205.0, mailed on Jan. 28, 2026, 7 pages, with English Translation.
Office Action in RU Appln. No. 2023103405, mailed on Jan. 14, 2025, 30 pages, with English Translation.
Office Action in SG Appln. No. 11202261692V, mailed on Aug. 12, 2025, 7 pages, with English Translation.
Office Action in TW Appln. No. 110126529, mailed on Mar. 24, 2025, 17 pages, with English Translation.
Office Action in VN Appln. No. 1-2023-00898, mailed on Jul. 3, 2025, 4 pages, with English Translation.
Ohba et al., "Mutant IDH1-Driven Cellular Transformation Increases RAD51-Mediated Homologous Recombination and Temozolomide Resistance," Cancer Research, 2014, 74(17):4836-4844.
Pansuriya et al., "Somatic Mosaic IDHI and IDH2 Mutations Are Associated With Enchondroma and Spindle Cell Hemangioma in Ollier Disease and Maffucci Syndrome," Nature Genetics, 43(12):1256-1261, Nov. 2011.
Parsons et al., "An Integrated Genomic Analysis of Human Glioblastoma Multiforme," Science, 321(5897):1807-1812, Sep. 2008.
Paschka et al., "IDH1 and IDH2 Mutations Are Frequent Genetic Alterations in Acute Myeloid Leukemia and Confer Adverse Prognosis in Cytogenetically Normal Acute Myeloid Leukemia With NPM1 Mutation Without FLT3 Internal Tandem Duplication," Journal of Clinical Oncology 28(22):3636-3643, Aug. 2010.
Shibata et al., "Mutant IDHI Confers an In Vivo Growth in a Melanoma Cell Line With BRAF Mutation," American Journal of Pathology, 178(3):1395-1402, Mar. 2011.
Shohji et al., "Ti(O-i-Pr)4/Me3SiCl/Mg-Mediated Reductive Cleavage of Sulfonamides and Sulfonates to Amines and Alcohols," Organic Letters, Apr. 2011, 13(10):2626-2629.
Sjoblom et al., "The Concensus Coding Sequences of Human Breast and Colorectal Cancers," Science, 314(5797):268-274, Oct. 2006.
Supplementary European Search Report and European Search Opinion dated Apr. 3, 2024 issued by the European Patent Office for Application No. 21845205.0.

(56) References Cited

OTHER PUBLICATIONS

Takata, "Cocrystal Screening and Its Application in Improvement of Physiochemical Properties of APIs," Pharm Tech Japan. 2009. 25(12):155-166, 12 pages (with English abstract).
Talukdar et al., "Low-Valent Titanium Mediated Reductive Deoxygenation of Carbonyls to Methylenes via Carbon-Nitrogen Bond Cleavage in N-(Arylmethyl) Anilines," Synthetic Communications, Aug. 1996, 26(6):1051-1056.
Tefferi et al., "IDHI and IDH2 Mutation Studies in 1473 Patients With Chronic-, Fibrotic- or Blast-Phase Essential Thrombocythemia, Polycythemia Vera or Myelofibrosis," Leukemia, 24(7):1302-1309, Jul. 2010.
Temodar (temozolomide), "Highlights of prescribing information," FDA Label, Nov. 2019, 21 pages.
Vissers et al., "Whole-Exome Sequencing Detects Somatic Mutations of IDHI in Metaphyseal Chondromatosis With D-2-Hydroxyglutaric Aciduria (MC-HGA)," American Journal of Medical Genetics, Part A 155A(11):2609-2616, Nov. 2011.
Wang et al., "N-Alkylation-Initiated Redox-Neutral [5 + 2] Annulation of 3-Alkylindoles with o-Aminobenzaldehydes: Access to Indole-1,2-Fused 1,4-Benzodiazepines," Organic Letters, Nov. 2019, 21(22):8904-8908.
Ward et al., "Identification of Additional IDH Mutations Associated With Oncometabolite R(-)-2-Hydroxyglutarate Production," Oncogene, 31(19):2491-2498, May 2012.
Ward et al., "The Common Feature of Leukemia-Associated IDH1 and IDH2 Mutations Is a Neomorphic Enzyme Activity Converting a-Ketoglutarate to 2-Hydroxyglutarate," Cancer Cell, 17(3):225-234, Mar. 2010.
Yan et al., "IDHI and IDH2 Mutations in Gliomas," New England Journal of Medicine, 360(8):765-773, Feb. 2009.
Yang et al., "IDHI and IDH2 Mutations in Tumorigenesis: Mechanistic Insights and Clinical Perspectives," Clinical Cancer Research, 18(20):5562-5571, Oct. 2012.

* cited by examiner

Feed + water for injection
Feed + temozolomide solution 0.75 mg/kg
Feed + temozolomide solution 1.5 mg/kg
Feed containing test compound + water for injection
Feed containing test compound + temozolomide solution 0.75 mg/kg
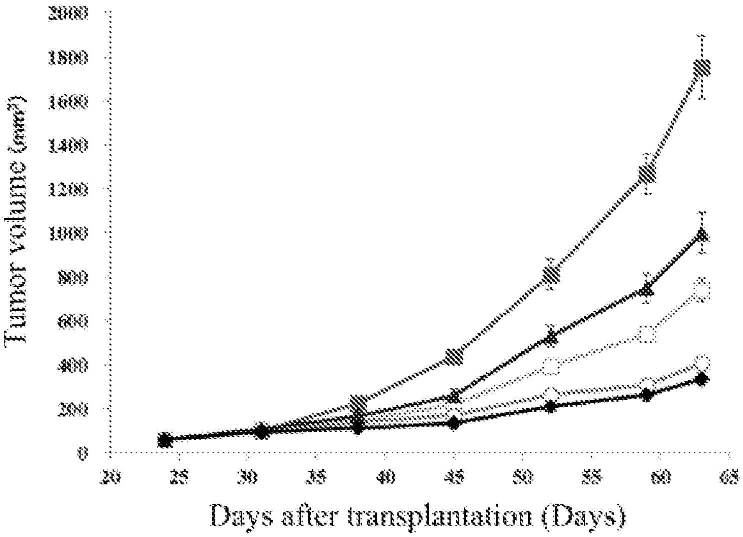

COMBINATION PHARMACEUTICAL OF TEMOZOLOMIDE AND MUTANT IDHI ENZYME INHIBITOR

CROSS REFERENCE TO RELATED APPLICATIONS

This application is a U.S. national phase filing under 35 U.S.C. § 371 of International Application No. PCT/JP2021/027070, filed Jul. 20, 2021, which claims priority to Japanese Application No. 2020-124331, filed Jul. 21, 2020, the contents of which are incorporated herein by reference in their entirety.

TECHNICAL FIELD

The present invention relates to a combination pharmaceutical containing temozolomide and a mutant IDH1 enzyme inhibitor and having excellent antitumor activity.

BACKGROUND TECHNOLOGY

Temozolomide is an antitumor agent classified as an alkylating agent and is used as a treatment for brain tumors, particularly glioma. In the treatment of brain tumors, it is necessary for the administered drug to pass through the blood-brain barrier, but very few drugs are effective against brain tumors because most anticancer drugs used for tumors of the body trunk cannot pass through the blood-brain barrier. Temozolomide has been shown to be effective in the treatment of a variety of malignant gliomas, including glioblastoma, the most aggressive form of glioma.

Grade II and grade III malignant gliomas have a slower tumor growth rate than glioblastomas, and have a relatively longer prognosis from the time of initial diagnosis. Although radiation therapy or chemoradiation is commonly used after surgical removal of these low-grade gliomas to prevent recurrence, these treatments cannot eradicate the microscopic cancer cells that have invaded the normal brain and will eventually recur. These cancer cells often change to a more malignant tumor at recurrence, and the prognosis after recurrence is extremely poor, such as with glioblastoma. Temozolomide is used for initial or recurrent treatment, but because it is an alkylating agent, it has been reported to have a dose-dependent risk of developing secondary cancers, and long-term, high-dose administration may not be appropriate (non-patent literature 1).

Isocitrate dehydrogenases (IDHs) are metabolic enzymes that convert isocitrate to α-ketoglutarate (α-KG). There are three types of IDHs: IDH1, IDH2, and IDH3. IDH1 and IDH2 use nicotinamide adenine dinucleotide phosphate (NADP+) as a cofactor and produce reduced NADPH in the reaction process. IDH3 uses nicotinamide adenine dinucleotide (NAD+) as a cofactor and creates a TCA cycle (tricarboxylic acid cycle).

Point mutations in the IDH1 gene are found in brain tumors such as glioma, acute myelogenous leukemia, myelodysplastic syndromes, myeloproliferative tumors, peripheral T-cell lymphoma, chondrosarcoma, osteosarcoma, cholangiocarcinoma, primitive neuroectodermal tumors, B lymphoblastic lymphoma, malignant melanoma, prostate cancer, colorectal cancer, and thyroid cancer. Among these, missense mutations of arginine 132 residue (R132), such as substitution of histidine (R132H) and cysteine (R132C), are frequently observed. The mutant IDH1 enzyme has reduced activity compared to the original IDH1 enzyme and has a new function that converts α-KG to 2-hydroxyglutarate (2-HG). Indeed, tumor cells with IDH1 mutations show a marked increase in the amount of 2-HG. High concentrations of 2-HG are known to inhibit α-KG-dependent dioxygenases, such as DNA and histone demethylases, resulting in epigenetic changes such as increased DNA methylation in cells, which is thought to have a significant impact on tumor progression. Mutant IDH1 enzyme inhibitors include, for example, (2E)-3-(1-{[5-(2-fluoropropane-2-yl]-3-(2,4,6-trichlorophenyl)-1,2-oxazol-4-yl]carbonyl}-3-methyl-1H-indole-4-yl)prop-2-enoic acid (Patent document 1), Ivosidenib (Patent document 2), compounds such as AG-881, BAY1436032, IDH305, FT-2102, LY3410738 or pharmaceutically acceptable salts of those compounds, and the like.

BACKGROUND TECHNOLOGY DOCUMENTS

Patent Documents

[Patent Document 1] WO2016/052697
[Patent Document 2] WO2013/107291

Nonpatent Documents

[Non-patent document 1] Momota S, et. al, Neuro Oncol. 15: 1445-1450, (2013).

SUMMARY OF THE INVENTION

Problem to be Solved by the Invention

The problem of the present invention is to provide a combination pharmaceutical having excellent efficacy against cancers with IDH1 gene mutations, wherein the dosage of temozolomide can be reduced without reducing the antitumor effect.

Means for Solving the Problem

The present inventors conducted a thorough investigation to solve the problem. As a result, it was determined that a combination of temozolomide and a mutant IDH1 enzyme inhibitor can reduce the dosage of temozolomide without decreasing the antitumor effect, leading to completion of the present invention. The present invention relates to the following (1) to (32).

(1) A pharmaceutical composition for use in the treatment of cancer, containing: a mutant IDH1 enzyme inhibitor administered in combination with temozolomide.

(2) The pharmaceutical composition according to (1), administered simultaneously or at different times with temozolomide.

(3) The pharmaceutical composition according to (1) or (2), wherein the mutant IDH1 enzyme inhibitor is one type selected from:

(i) a compound expressed by the following Formula (I), or a pharmaceutically acceptable salt thereof;

(I)

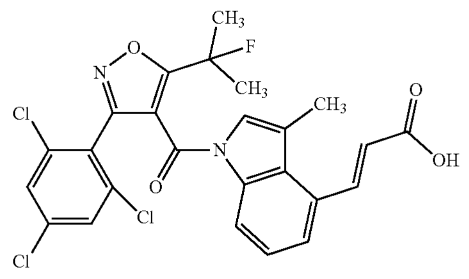

(ii) Ivosidenib or a pharmaceutically acceptable salt thereof;
(iii) AG-881 or a pharmaceutically acceptable salt thereof;
(iv) BAY1436032 or a pharmaceutically acceptable salt thereof,
(v) IDH 305 or a pharmaceutically acceptable salt thereof; and
(vi) FT-2102 or a pharmaceutically acceptable salt thereof.

(4) The pharmaceutical composition according to any one of (1) to (3), wherein the mutant IDH1 enzyme inhibitor is a compound expressed by Formula (I) above or a pharmaceutically acceptable salt thereof.

(5) The pharmaceutical composition according to any one of (1) to (3), wherein the mutant IDH1 enzyme inhibitor is a tert-butylamine salt of a compound expressed by Formula (I) above.

(6) The pharmaceutical composition according to any one of (1) to (5), wherein the cancer is a cancer having an IDH1 gene mutation.

(7) The pharmaceutical composition according to any one of (1) to (6), wherein the cancer is a brain tumor.

(8) The pharmaceutical composition according to (7), wherein the brain tumor is a glioma.

(9) A pharmaceutical composition for use in the treatment of cancer, containing: a mutant IDH1 enzyme inhibitor administered in combination with temozolomide.

(10) The pharmaceutical composition according to (9), wherein the mutant IDH1 enzyme inhibitor and temozolomide are administered simultaneously or at different times.

(11) The pharmaceutical composition according to (9) or (10), wherein the mutant IDH1 enzyme inhibitor is one type selected from:

(i) a compound expressed by Formula (I) above, or a pharmaceutically acceptable salt thereof;
(ii) Ivosidenib or a pharmaceutically acceptable salt thereof;
(iii) AG-881 or a pharmaceutically acceptable salt thereof;
(iv) BAY1436032 or a pharmaceutically acceptable salt thereof;
(v) IDH 305 or a pharmaceutically acceptable salt thereof; and
(vi) FT-2102 or a pharmaceutically acceptable salt thereof.

(12) The pharmaceutical composition according to any one of (9) to (11), wherein the mutant IDH1 enzyme inhibitor is a compound expressed by Formula (I) above or a pharmaceutically acceptable salt thereof.

(13) The pharmaceutical composition according to any one of (9) to (11), wherein the mutant IDH1 enzyme inhibitor is a tert-butylamine salt of a compound expressed by Formula (I) above.

(14) The pharmaceutical composition according to any one of (9) to (13), wherein the cancer is a cancer having an IDH1 gene mutation.

(15) The pharmaceutical composition according to any one of (9) to (14), wherein the cancer is a brain tumor.

(16) The pharmaceutical composition according to (15), wherein the brain tumor is a glioma.

(17) A method of treating cancer, including: administering a mutant IDH1 enzyme inhibitor in combination with temozolomide.

(18) The method of treating cancer according to (17), wherein the mutant IDH1 enzyme inhibitor and temozolomide are administered simultaneously or at different times.

(19) The method of treating cancer according to (17) or (18), wherein the mutant IDH1 enzyme inhibitor is one type selected from:

(i) a compound expressed by Formula (I) above, or a pharmaceutically acceptable salt thereof;
(ii) Ivosidenib or a pharmaceutically acceptable salt thereof;
(iii) AG-881 or a pharmaceutically acceptable salt thereof;
(iv) BAY1436032 or a pharmaceutically acceptable salt thereof;
(v) IDH 305 or a pharmaceutically acceptable salt thereof;
(vi) FT-2102 or a pharmaceutically acceptable salt thereof; and
(vii) LY3410738 or a pharmaceutically acceptable salt thereof.

(20) The method of treating cancer according to any one of (17) to (19), wherein the mutant IDH1 enzyme inhibitor is a compound expressed by Formula (I) above or a pharmaceutically acceptable salt thereof.

(21) The method of treating cancer according to any one of (17) to (20), wherein the mutant IDH1 enzyme inhibitor is a tert-butylamine salt of a compound expressed by Formula (I) above.

(22) The method of treating a cancer according to any one of (17) to (21), wherein the cancer is a cancer having an IDH1 gene mutation.

(23) The method of treating a cancer according to any one of (17) to (22), wherein the cancer is a brain tumor.

(24) The method of treating a cancer according to (23), wherein the brain tumor is a glioma.

(25) A pharmaceutical composition for use in the treatment of cancer, containing a mutant IDH1 enzyme inhibitor and temozolomide.

(26) A pharmaceutical composition for use in the treatment of cancer, containing a pharmaceutical composition containing a mutant IDH1 enzyme inhibitor in combination with a pharmaceutical composition containing temozolomide.

(27) The method of treating cancer according to (25) or (26), wherein the mutant IDH1 enzyme inhibitor is one type selected from:

(i) a compound expressed by Formula (I) above, or a pharmaceutically acceptable salt thereof;
(ii) Ivosidenib or a pharmaceutically acceptable salt thereof;
(iii) AG-881 or a pharmaceutically acceptable salt thereof;
(iv) BAY1436032 or a pharmaceutically acceptable salt thereof;
(v) IDH 305 or a pharmaceutically acceptable salt thereof;
(vi) FT-2102 or a pharmaceutically acceptable salt thereof; and
(vii) LY3410738 or a pharmaceutically acceptable salt thereof.

(28) The pharmaceutical composition according to any one of (25) to (27), wherein the mutant IDH1 enzyme inhibitor is a compound expressed by Formula (I) above or a pharmaceutically acceptable salt thereof.

(29) The pharmaceutical composition according to any one of (25) to (27), wherein the mutant IDH1 enzyme inhibitor is a tert-butylamine salt of a compound expressed by Formula (I) above.

(30) The pharmaceutical composition according to any one of (25) to (29), wherein the cancer is a cancer having an IDH1 gene mutation.

(31) The pharmaceutical composition according to any one of (25) to (30), wherein the cancer is a brain tumor.

(32) The pharmaceutical composition according to (31), wherein the brain tumor is a glioma.

Effect of the Invention

The present invention enables a combination of temozolomide and a mutant IDH1 enzyme inhibitor to provide a therapeutic agent with enhanced antitumor activity and superior efficacy against cancers with IDH1 gene mutations, while reducing the dosage of temozolomide.

BRIEF DESCRIPTION OF THE DRAWINGS

FIG. 1 shows the antitumor effects of each drug as a single agent and when used in combination.

DESCRIPTION OF THE PREFERRED EMBODIMENTS

The pharmaceutical compositions of the present invention are characterized in that the mutant IDH1 enzyme inhibitor and temozolomide are administered in combination. In the present invention, "administered in combination" includes administering the active ingredients, the mutant IDH1 enzyme inhibitor and temozolomide, in the form of their respective single formulations, simultaneously or at different times, by the same or different administration routes. The number of times each component is administered may be the same or different. Thus, the pharmaceutical compositions of the present invention may be a fixed dose formulation containing two active ingredients in one composition, or a combination formulation containing two active ingredients in separate compositions.

In the present invention, the "mutant IDH1 enzyme inhibitor" is not particularly limited to a compound that inhibits the activity of the mutant IDH1 enzyme. Evaluation of the inhibition of the activity of the mutant IDH1 enzyme can be performed using a method known to one skilled in the art (for example, the method disclosed in WO2016/052697 of detecting the inhibitory effect of mutant IDH1 enzyme on the conversion reaction of 2-oxoglutarate and NADPH to D-2-hydroxyglutarate and NADP+ using a WST-8 assay).

The "mutant IDH1 enzyme inhibitor" of the present invention includes, for example, the following:

(i) a compound expressed by formula (I) above, or a pharmaceutically acceptable salt thereof;

(ii) Ivosidenib or a pharmaceutically acceptable salt thereof;

(iii) AG-881 or a pharmaceutically acceptable salt thereof;

(iv) BAY1436032 or a pharmaceutically acceptable salt thereof, (v) IDH 305 or a pharmaceutically acceptable salt thereof;

(vi) FT-2102 or a pharmaceutically acceptable salt thereof, and (vii) LY3410738 or a pharmaceutically acceptable salt thereof.

The compound of the present invention, expressed by Formula (I), is also referred to as (2E)-3-(1-{[5-(2-fluoropropan-2-yl)-3-(2,4,6-trichlorophenyl)-1,2-oxazol-4-yl]carbonyl)-3-methyl-1H-indol-4-yl)prop-2-enoic acid. The compound shown in Formula (I) can be produced, for example, according to the method described in WO2016/052697. WO2016/052697 is incorporated herein in its entirety by reference.

The pharmaceutically acceptable salt of the compound of Formula (I) of the present invention is most preferably a tert-butylamine salt of (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid (hereinafter referred to as the "test compound"). The compound is also referred to by another name: mono(2-methylpropan-2-ammonium)(2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoate.

In the present invention, "Ivosidenib" refers to (2S)—N-[(1S)-1-(2-chlorophenyl)-2-[(3,3-difluorodichlobutyl) amino]-2-oxoethyl]-1-(4-cyanopyridine-2-yl)-N-(5-fluoro-pyridin-3-yl)-5-oxopyrrolidine-2-carboxamide. A drug that contains Ivosidenib as an active ingredient is marketed under the trade name "Tibsovo." Ivosidenib can be produced, for example, according to the method described in WO2013/107291. WO2013/107291 is incorporated herein in its entirety by reference.

In the present invention, "AG881" refers to 6-(6-chloro-pyridin-2-yl)-2-N,4-N-bis[(2R)-1,1,1-trifluoropropan-2-yl]-1,3,5-triazine-2,4-diamine. AG-881 is also known as Vorasidenib. AG-881 can be produced, for example, according to the method described in WO2015/003640. WO2015/003640 is incorporated herein in its entirety by reference.

In the present invention, "BAY1436032" refers to 3-(2-((4-(trifluoromethoxy)phenyl)amino)-1-((1R,5R)-3,3,5-trimethylcyclohexyl)-1H-benzo[d]imidazol-5-yl)propanoic acid. BAY1436032 can be produced, for example, according to the methods described in WO2015/121210 and WO2017/016992. WO2015/121210 and WO2017/016992 are incorporated herein in entirety by reference.

In the present invention, "IDH305" refers to (R)-4-((S)-1-fluoroethyl)-3-(2-(((S)-1-(4-methyl-2'-(trifluoromethyl)-[3,4'-bipyridine]-6-yl)ethyl)amino)pyrimidin-4-yl)oxazolin-2-one. IDH 305 can be produced, for example, according to the method described in WO 2014/141104. WO2014/141104 is incorporated herein in its entirety by reference.

In the present invention, "FT2102" can be produced, for example, according to the method described in WO2016/044787. WO2016/044787 is incorporated herein in its entirety by reference.

In the present invention, "LY3410738" is a drug for which clinical trials are being conducted in Japan, the U.S. and other countries (Clinical Research Information Portal Site Clinical Research Protocol Number: jRCT2031200178, ClinicalTrials.gov Identifier: NCT04603001).

In the present invention, "pharmaceutically acceptable salt" refers to a salt that does not have significant toxicity and can be used as a pharmaceutical composition. Compounds having an acidic substituent can be made into a salt by reacting with a base. Examples include: alkali metal salts such as sodium salt, potassium salt, and lithium salt; alkaline earth metal salts such as calcium salt and magnesium salt; metal salts such as aluminum salt and iron salt; inorganic salts such as ammonium salt; amine salts such as tert-butylamine salt, tert octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt dicyclohexylamine salt, N, N'-dibenzylethylenediamine salt, chloroprocaine salt, procaine salt, diethanolamine salt, N-benzylphenethylamine salt, piperazine salt, tetramethylammonium salt, tris(hydroxymethyl)aminomethane salt; and amino acid salts such as glycine salt, lysine salt, arginine salt, ornithine salt, glutamate salt, and aspartate salt. However, there is no restriction to these salts.

A compound having a basic substituent can be made into a salt by reacting with an acid. Examples include: hydrohalides such as hydrofluoride, hydrochloride, hydrobromide, hydroiodide; inorganic acid salts such as nitrate, perchlorate, sulfate, phosphate; $C_1$ to $C_6$ alkylsulfonates such as methanesulfonate, trifluoromethanesulfonate, ethanesulfonate; arylsulfonates such as benzenesulfonate, p-toluenesulfonate; organic acid salts such as acetate, phosphate, fumarate, succinate, citrate, ascorbate, tartrate, oxalate, adipate, maleate; and amino acid salts such as glycine salt, lysine salt, arginine salt, ornithine salt, glutamate salt and aspartate salt.

In the present invention, the (i) compound expressed by Formula (I) above, or a pharmaceutically acceptable salt thereof;
(ii) Ivosidenib or a pharmaceutically acceptable salt thereof;
(iii) AG-881 or a pharmaceutically acceptable salt thereof;
(iv) BAY1436032 or a pharmaceutically acceptable salt thereof,
(v) IDH 305 or a pharmaceutically acceptable salt thereof;
(vi) FT-2102 or a pharmaceutically acceptable salt thereof, and
(vii) LY3410738 or a pharmaceutically acceptable salt thereof, may be left in the air or recrystallized to incorporate water molecules and become a hydrate, and these hydrates are also included in the present invention.

In the present invention, the (i) compound expressed by Formula (I) above, or a pharmaceutically acceptable salt thereof;
(ii) Ivosidenib or a pharmaceutically acceptable salt thereof;
(iii) AG-881 or a pharmaceutically acceptable salt thereof;
(iv) BAY1436032 or a pharmaceutically acceptable salt thereof,
(v) IDH 305 or a pharmaceutically acceptable salt thereof;
(vi) FT-2102 or a pharmaceutically acceptable salt thereof, and
(vii) LY3410738 or pharmaceutically acceptable salts thereof, may absorb certain solvents and become solvates by being left in a solvent or by recrystallization, and such solvates are also included in the present invention.

As used herein, the term “cancer” refers to all malignancies.

In this specification, “glioma” refers to brain tumors that originate from glial cells, which are the supporting tissue of brain neurons. Gliomas are also known as gliomas.

Gliomas can be classified according to the pathological diagnosis. For example, the 3rd edition of the Brain Tumor Treatment Protocol (Kinbara Publishing Co., Ltd.) classifies brain tumors based on the WHO classification, 4th edition (WHO 2007). The major classifications include: A. astrocytic tumors such as pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma, giant cell glioblastoma, gliosarcoma, and gliomatosis cerebri; B oligodendroglial tumors: oligodendroglioma, anaplastic oligoastrocytoma; C. ependymal tumors: subependymoma, myxopapillary ependymoma, ependymoma, cellular, papillary, clear cell, tanycytic, and anaplastic ependymoma, and the like.

Furthermore, they are also classified into four grades (WHO Grade) according to the clinical grade. Grade I includes, for example, subependymal giant cell astrocytoma, pilocytic astrocytoma, subependymoma, myxopapillary ependymoma, and the like. Grade II includes, for example, pilomyxoid astrocytoma, diffuse astrocytoma, pleomorphic xanthoastrocytoma, oligodendroglioma, oligoastrocytoma, ependymoma, and the like. Grade III includes, for example, anaplastic astrocytoma, anaplastic oligoastrocytoma, anaplastic oligoastrocytoma, anaplastic ependymoma, and the like. Grade IV, for example, includes glioblastoma, giant cell glioblastoma, gliosarcoma, and the like.

IDH1 mutations of glioma are less frequent in primary glioblastoma, but more frequent at about 80% in WHO grade II and grade III gliomas and secondary glioblastoma. Furthermore, in gliomas with IDH1 mutations, IDH1 mutations have been shown to occur at an early stage and are thought to play an important role in tumor development and subsequent accumulation of genetic abnormalities.

The mutations in the “mutant IDH1” in the present invention include, but are not limited to, mutations in the 132nd position arginine (hereinafter referred to as R132), mutations in the 97th position glycine (hereinafter referred to as G97), mutations in the 100th position arginine (hereinafter referred to as R100), mutations in the 133rd position histidine (hereinafter referred to as H133), and mutations in the 134th position alanine (hereinafter referred to as A134). The mutations of R132 include, but are not limited to, mutations to histidine (R132H), mutations to cytosine (R132C), mutations to leucine (R132L), mutations to serine (R132S), mutations to glycine (R132G), and mutations to valine (R132V). The compounds expressed by Formula (I) of the present invention, or pharmaceutically acceptable salts thereof, are particularly suitable as inhibitors of the R132 variant of IDH1.

The amino acid sequence of a typical human wild IDH1 is listed in Genebank NP_005887.2 and UniprotKB 075874.

The presence of IDH1 mutations can be determined by commonly known pathological methods such as analyzing the patient's test tissue (for example, collected by blood sampling, biopsy, and the like) using Western blot, ELISA, DNA chip, FISH assay, tissue immunostaining, and other known genetic analysis methods (for example, Sanger sequencing analysis, next-generation DNA sequencing analysis (NGS), PCR, LCR (Ligase chain reaction), SDA (Strand displacement amplification), NASBA (Nucleic acid sequence-based amplification), ICAN (Isothermal and chineric primer-initiated amplification), LAMP (Loop-mediated isothermal amplification), and the like.

As used herein, “temozolomide” is an anticancer agent classified as an alkylating agent and is also referred to as 3-methyl-4-oxo-3,4-dihydromidazo[5,1-d][1,2,3,5]tetrazine-8-carboxamide. It is used around the world under the trade name “Temodar.”

The term “alkylating agent” as used herein refers to a substance that acts as an anticancer agent by alkylating the DNA of cancer cells and preventing cell proliferation.

In addition to temozolomide and mutant IDH1 enzyme inhibitors, the present invention may be used in combination with other antitumor agents and other therapies (for example, radiation therapy, immunotherapy).

In the present invention, when the mutant IDH1 enzyme inhibitor and/or temozolomide is prepared as a pharmaceutical composition, examples of pharmaceutically acceptable carriers that can be used include sterile water or saline, vegetable oil, solvents, base agents, emulsifiers, suspending agents, surfactants, stabilizers, flavoring agents, aromatic agents, excipients, vehicles, preservatives, binders, diluents, isotonic agents, pain eliminating agents, bulking agents, disintegrating agents, buffering agents, coating agents, lubricants, coloring agents, sweetening agents, viscous agents, taste and odor correcting agents, dissolution aids, or other additives, but not limited thereto. The compounds of the present invention or pharmaceutically acceptable salts thereof can be prepared in various forms, such as tablets, sprays, granules, capsules, and liquids, depending on the therapeutic purpose and the like. They can also be administered, for example, in the form of a liposomal delivery system. These liposomes can also be supplemented with the aforementioned auxiliary portions (for example, antibodies, ligands, and the like) that enhance therapeutically useful properties.

The present invention also relates to a method of treating cancer, including administering a mutant IDH1 enzyme inhibitor in combination with temozolomide.

"Patients" to whom a mutant IDH1 enzyme inhibitor can be administered in combination with temozolomide include not only individuals who have cancer, but also individuals undergoing or recovering from treatment for cancer (for example, individuals whose cancer may recur).

Administration to the patient may be by oral or parenteral route. Parenteral administration includes, for example, intravenous, arterial, intramuscular, intrathoracic, intraperitoneal, and direct administration to the target site (for example, a tumor).

There is no restriction on the dosage, as long as the dosage is effective in treating the target disease, and may be selected based on the patient's age, weight, symptoms, health condition, disease progression, and the like. There is no restriction as to the frequency of administration, and it may be selected according to the purpose, and for example, a daily dosage can be administered once per day, or the dose can be subdivided and administered. When the agents of the present invention are administered to humans, the dosage of each active ingredient is usually in a range from about 0.01 mg/kg body weight to about 500 mg/kg body weight per day, preferably from about 0.1 mg/kg body weight to about 100 mg/kg body weight per day. When administered to humans, the frequency is preferably once per day, or two to four divided doses are repeated administered at appropriate intervals. In addition, with the present invention, by administering the temozolomide in combination with a mutant IDH1 enzyme inhibitor, the dose of temozolomide can be reduced compared to that normally used (when administered alone), preferably by ⅕ to ⅘, more preferably by ¼ to ¾, even more preferably by ⅓ to ⅔, yet more preferably by ½ (for example, it can be reduced to ⅖ to ⅗ or ½).

In the present invention, "treatment" includes not only complete recovery from cancer, but also inhibition of cancer progression (inhibition of growth of cancerous tissue, reduction of cancerous tissue, and the like), inhibition of cancer development (inhibition of secondary cancer development, inhibition of cancer recurrence, and the like), and alleviation of cancer-related symptoms.

The composition of the present invention can be used not only in the form of a pharmaceutical composition as described above, but also as a reagent. With the present invention, when the mutant IDH1 enzyme inhibitor and/or temozolomide is prepared as a reagent, other components acceptable as reagents, such as sterile water or saline, buffers, and preservatives, may be included as necessary. Such reagents can be administered to a target (for example, cells or fractions thereof, tissues, experimental animals, and the like) at a dosage appropriate for the purpose, for example, to inhibit mutant IDH1, to inhibit production of 2-HG, and to inhibit tumor growth.

EXAMPLES

The present invention will be described below in further detail using examples, but the scope of the present invention is not limited thereto.

(Example) Measurement of Antitumor Activity in a Mouse Model of Glioblastoma A1074 Transplanted from a Human Patient with IDH1 R132H Mutation Glioblastoma A1074 from a human patient with IDH1 R132H mutation was divided into 4-mm pieces and implanted subcutaneously in the right axillary region in 96 NSG mice (Charles River, Japan). When appropriate, the mass was measured using calipers and the tumor volume ($mm^3$) was calculated using the formula (long diameter)×(short diameter)$^2$/2 and used to confirm the growth of the mass and the drug effect.

On the 24th day after transplantation, the following groups were selected according to the tumor volume: feed (CRF-1 (Oriental Yeast Industry Co., Ltd.))+water for injection group, feed+temozolomide solution (0.75 mg/kg) group, feed+temozolomide solution (1.5 mg/kg) group, feed containing the test compound (CRF-1 based on 0.34% (by weight) of the test compound)+water for injection group, and the test compound formula feed+temozolomide aqueous solution (0.75 mg/kg) group, a total of 5 groups, 12 cases in each group. Water for injection or temozolomide solution was administered orally for 5 consecutive days after grouping. The test compounds were administered as test compound formulated diet for 40 days. As mentioned above, the compound (mutant IDH1 enzyme inhibitor) that was used in this study was the tert-butylamine salt of (2E)-3-(1-{[5-(2-fluoropropane-2-yl)-3-(2,4,6-trichlorophenyl)-1,2-oxazole-4-yl]carbonyl}-3-methyl-1H-indole-4-yl)prop-2-enoic acid, which was synthesized and used by the method described in [Example 168] of WO2016/052697.

The tumor growth inhibition rate (%) was calculated by the following formula.

Tumor growth inhibition rate (%)={1−(tumor volume of each treatment group at each time point)/(tumor volume of feed+water for injection group)}×100.

Tumor volumes during 40 days after grouping are shown in Table 1 and FIG. 1. The combination of the test compound with temozolomide showed stronger inhibition of tumor growth while reducing the dose of temozolomide.

TABLE 1

| Tumor Growth Inhibition Rate (%) on Day 63 Compared to the "Feed + Water for Injection" Group | |
|---|---|
| Feed + temozolomide solution 0.75 mg/kg | 58% |
| Feed + temozolomide solution 1.5 mg/kg | 77% |
| Feed containing test compound + water for injection | 43% |
| Feed containing test compound + temozolomide solution 0.75 mg/kg | 81% |

INDUSTRIAL APPLICABILITY

As described above, with the present invention, the combination of temozolomide with a mutant IDH1 enzyme inhibitor enables a reduction in the dosage of temozolomide without reducing the antitumor effect. By extension, the risk of developing temozolomide dose-dependent secondary cancers can also be reduced. Therefore, the present invention is particularly usable in the medical field as a combination pharmaceutical having an excellent effect on cancers having IDH1 gene mutations.

The invention claimed is:

1. A method of treating a patient with a brain tumor having an IDH1 mutation, comprising administering to the patient an effective amount of a mutant IDH1 enzyme inhibitor in combination with an effective amount of temozolomide, wherein the mutant IDH1 enzyme inhibitor is a compound of Formula (I) or a pharmaceutically acceptable salt thereof:

(I)

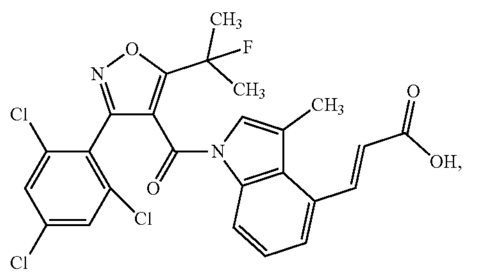

and wherein the brain tumor is a brain tumor to which temozolomide is effective.

2. The method of claim 1, wherein the mutant IDH1 enzyme inhibitor and temozolomide are administered simultaneously.

3. The method of claim 1, wherein the mutant IDH1 enzyme inhibitor and temozolomide are administered at different times.

4. The method of claim 1, wherein the mutant IDH1 enzyme inhibitor is a tert-butylamine salt of the compound of Formula (I).

5. The method of claim 1, wherein the brain tumor is glioma.

6. The method of claim 1, wherein the IDH1 mutation is R132H, R132C, R132L, R132S, R132G, or R132V.

7. The method of claim 1, wherein the IDH1 mutation is R132C mutation.

8. The method of claim 1, wherein the IDH1 mutation is R132H mutation.

9. The method of claim 1, wherein the mutant IDH1 enzyme inhibitor is the compound of Formula (I).

10. The method of claim 1, wherein the mutant IDH1 enzyme inhibitor is a pharmaceutically acceptable salt of the compound of Formula (I).

* * * * *